United States Patent [19]
Johnson

[11] Patent Number: 4,576,178
[45] Date of Patent: Mar. 18, 1986

[54] AUDIO SIGNAL GENERATOR

[76] Inventor: David Johnson, 436 E. 69th St., New York, N.Y. 10021

[21] Appl. No.: 479,203

[22] Filed: Mar. 28, 1983

[51] Int. Cl.$^4$ ............................................. A61B 5/02
[52] U.S. Cl. ................... 128/670; 128/696; 128/700; 128/701; 324/140 R; 340/870.18; 381/56; 367/116
[58] Field of Search ............. 128/670, 700, 701, 706, 128/710, 715, 631, 696; 340/870.11, 870.18; 324/140 R; 381/56; 367/116, 135

[56] References Cited

U.S. PATENT DOCUMENTS

| | | | |
|---|---|---|---|
| 3,199,508 | 8/1965 | Roth | 128/902 |
| 3,215,136 | 11/1965 | Holter et al. | 128/701 |
| 3,229,687 | 1/1966 | Holter et al. | 128/701 |
| 3,338,234 | 8/1967 | Kleinerman et al. | 128/701 |
| 3,534,728 | 10/1970 | Barrows | 128/631 |
| 3,565,058 | 2/1971 | Mansfield | 128/701 |
| 3,572,316 | 3/1971 | Vogelman et al. | 128/690 |
| 3,613,670 | 10/1971 | Edenhofer | 128/701 |
| 3,615,162 | 10/1971 | Barber | 381/56 |
| 3,650,264 | 3/1972 | Janssen | 128/701 |
| 3,658,060 | 4/1972 | Eklof | 128/673 |
| 3,732,868 | 5/1973 | Willems et al. | 128/701 |
| 3,742,937 | 7/1973 | Manuel et al. | 128/701 |
| 3,760,100 | 9/1973 | Ragsdale et al. | 128/701 |
| 3,769,965 | 11/1973 | Raddi et al. | 128/701 |
| 3,830,227 | 8/1974 | Green | 128/701 |
| 3,895,316 | 7/1975 | Fein | 128/696 |
| 3,978,849 | 9/1976 | Geneen | 128/690 |
| 4,096,854 | 6/1978 | Perica et al. | 128/690 |
| 4,154,231 | 5/1979 | Russell | 128/700 |
| 4,319,081 | 3/1982 | Martin et al. | 381/56 |
| 4,408,613 | 10/1983 | Relyea | 128/670 |
| 4,424,511 | 1/1984 | Alberts, Jr. | 381/56 |

OTHER PUBLICATIONS

Cabot, An Economical Digitally Controlled Audio Level Indicator, Journal of the Audio Engineering Society, vol. 26, No. 1-2, Jan.-Feb. 1978, pp. 36-41.
Mackay et al., *Endoradiosonde*, Jun. 1957, Nature vol. 179, pp. 1239-1240.

*Primary Examiner*—Kyle L. Howell
*Assistant Examiner*—Ruth S. Smith
*Attorney, Agent, or Firm*—Robert Scobey

[57] ABSTRACT

A system is disclosed that includes an audio signal generator to provide a distinguishable audible output that varies in accordance with a monitored input. The audio signal generator varies a parameter of the audible output, such as frequency or amplitude, in n discrete steps corresponding to a range of variation in value of the monitored input. A plurality of different inputs may be monitored, and an audio signal generated therefrom having a plurality of different parameters, each of which corresponds to an individual one of the monitored inputs. The monitored inputs may be heart rate, systolic blood pressure, diastolic blood pressure, and body temperature. The audio signal produced may be composed of a series of recurring pulses, the parameters of which corresponding to the different monitored inputs are amplitude of each pulse, time duration of each pulse, time duration between the onset of successive pulses, and the frequency of the signal that defines each pulse.

10 Claims, 11 Drawing Figures

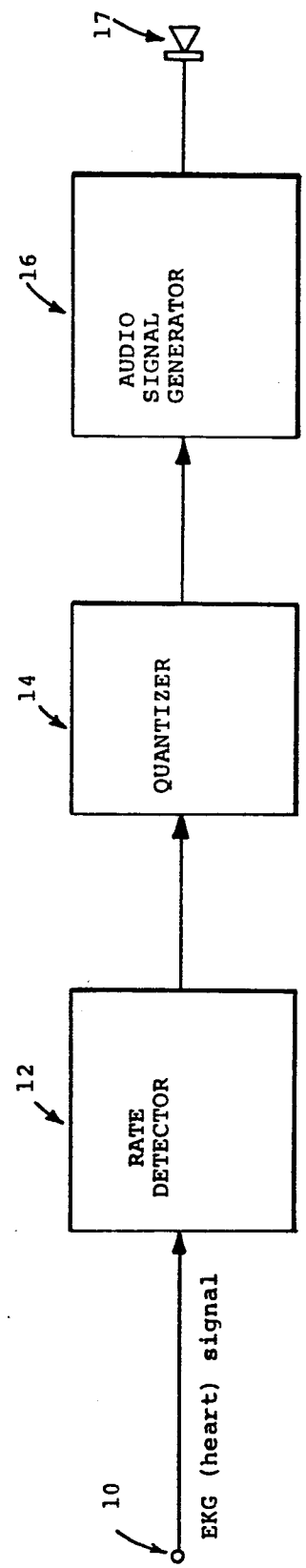

V to f Conversion Characteristics

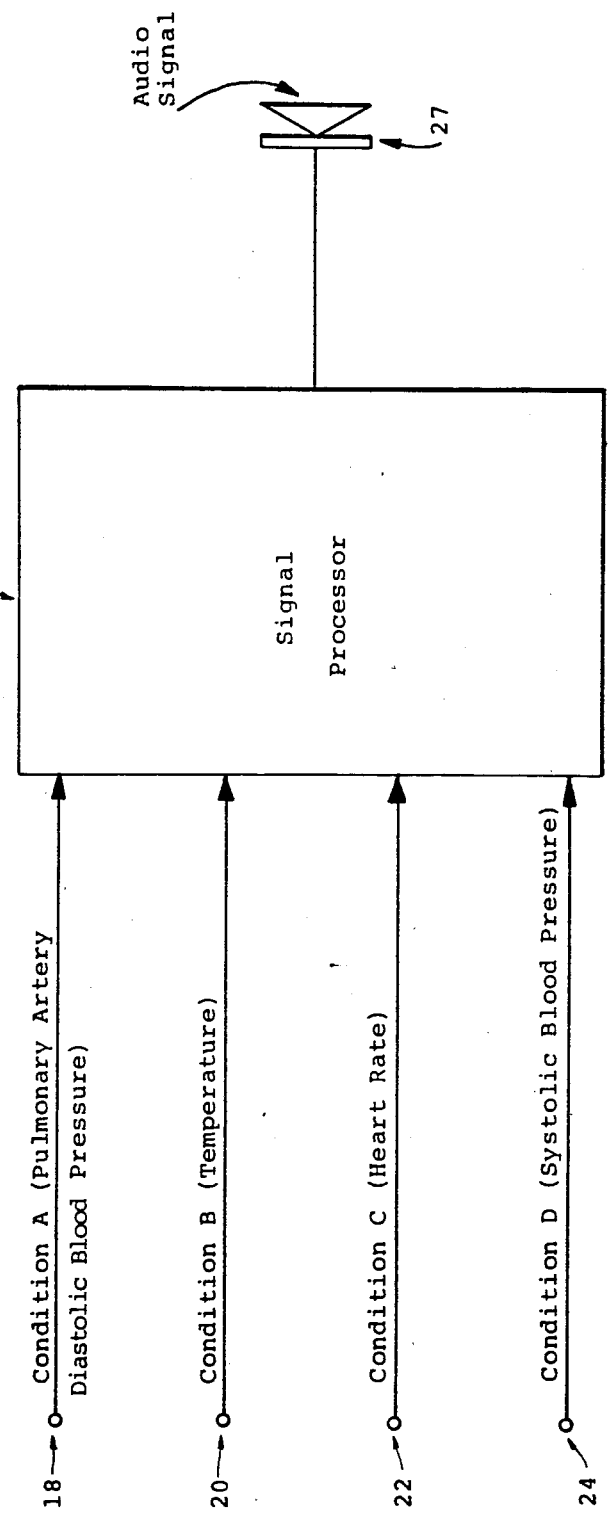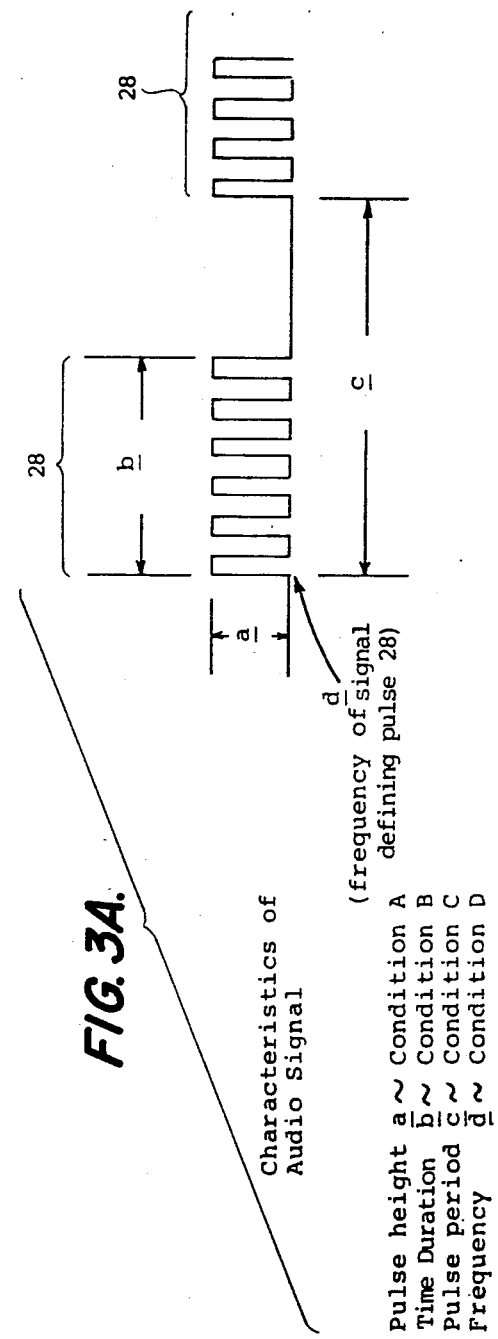

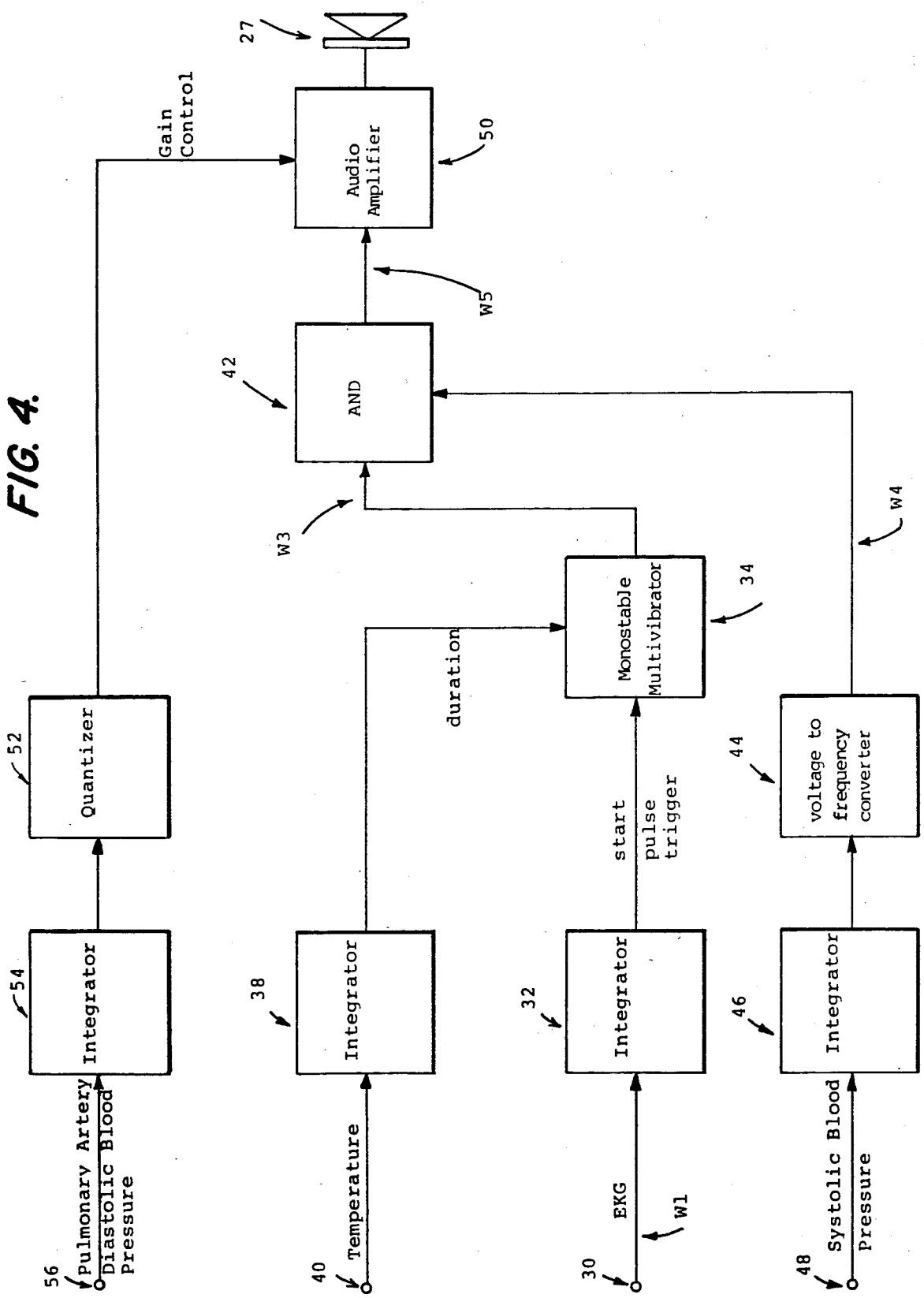

AUDIO SIGNAL GENERATOR

BACKGROUND AND BRIEF DESCRIPTION OF THE INVENTION

This invention relates to the monitoring of one or more inputs to develop an audible signal representative of the monitored input or inputs. It has particular application to the monitoring of body conditions, such as heart rate, systolic blood pressure, diastolic blood pressure, and body temperature, to name some examples, although it has broad application to the monitoring of any condition or conditions leading to the generation of a distinguishable audible output that varies in accordance with the monitored condition or conditions. The present invention is directed toward providing a distinguishable audible output that may be easily interpreted by an observer, without the need to visually inspect an instrument panel or to do anything beyond simply listening to the generated audible signal.

There are two principal aspects of the present invention; the first relates to the quantizing of a monitored input to produce an audible signal that varies in a plurality (n) of discrete steps that correspond to a range of variation in value of the monitored input. Thus, for example, if an electrocardiograph signal is monitored to develop an intermediate signal that is representative of the rate at which the heart is beating, that signal is quantized, for example, by use of a voltage to frequency converter having a step function input/output characteristic, to generate an audio signal that varies in a plurality (n) of discrete steps. Accordingly, a technician listening to the audible output signal will detect changes in frequency or amplitude, for example, as the output changes from one level to another, representing a change in the monitored electrocardiograph input. Since the output audible signal varies in step fashion, it is easier for the technician or physician to note a change, than if the output signal were to vary in continuous fashion. Small changes in a continuously varying output signal occurring over a relatively long period of time might not be noticed as any change at all.

A second aspect of the present invention lies in the monitoring of a plurality of different inputs. Again, to use the monitoring of body conditions as an example, if heart rate, systolic blood pressure, pulmonary artery diastolic blood pressure, and body temperature are all monitored, the present invention provides for the development of a distinguishable audible signal in which a plurality of different parameters of that signal each correspond to an individual one of the monitored inputs. Thus, for example, an audio signal may be generated composed of a series of recurring pulses, and the parameters of that signal corresponding to the monitored conditions are as follows:

(a) amplitude of each pulse (corresponding to pulmonary artery diastolic blood pressure),
(b) time duration of each pulse (corresponding to body temperature),
(c) time duration between the onset of successive pulses, i.e., the periodicity (corresponding to heart rate), and
(d) frequency of the signal defining each pulse (systolic blood pressure).

In such a system in which a plurality of different inputs are monitored, by varying an audible output parameter in accordance with the variation of an individual input, the technician or physician is able to continue his tasks and, by simply listening to the output signal, note when one of the monitored conditions changes. There is no need to visually inspect instrumentation, and the user may be easily trained to detect changes in any of the parameters of the audible output signal. In this regard, it should be noted that any one or more of those parameters may be quantized so that it varies in discrete steps corresponding to a range of monitored input variation, as described above.

The invention will be more completely understood by reference to the following detailed description of representative but presently preferred embodiments thereof.

BRIEF DESCRIPTION OF THE DRAWINGS

FIG. 1 is a block diagram of a system for providing a quantized output audio signal in accordance with the invention.

FIG. 3 is block diagram of a system in accordance with the invention for providing an audio signal having different parameters corresponding to different monitored inputs.

FIG. 3A is a waveform diagram of a typical audio signal generated by the system of FIG. 3.

FIG. 4 is a block diagram showing in more detail a system in accordance with FIG. 3.

DETAILED DESCRIPTION

Figure 2A:
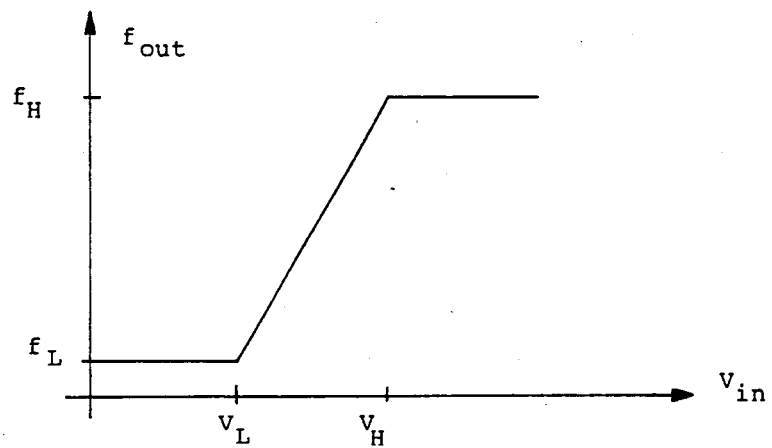
FIGS. 2A and 2B are voltage to frequency conversion characteristics useful in understanding the system of FIG. 1.

As noted above, the present invention involves a monitoring of one or more inuputs to provide a distinguishable audible output signal. While the following description of presently preferred embodiments is with respect to the monitoring of body conditions, this is simply representative, and the invention has broad application to the monitoring of any input condition or conditions leading to the generating of a suitable output signal which may be interpreted by the ear alone, without any visual reference to instrumentation.

As shown in FIG. 1, an electrocardiograph (EKG) signal from any conventional EKG monitor (not shown) is developed at input terminal 10. The signal is processed by a rate detector 12 to provide a signal having an output parameter such as frequency, to name an example, which represents the rate at which the heart is beating. That signal is passed to a quantizer 14 which quantizes the signal in n discrete steps corresponding to a range of input frequency variation. In other words, if the quantizer is supplied with a signal which continuously varies over an input frequency range representing, for example, 50 to 250 heart beats per minute, the quantizer develops an output signal which varies in discrete steps. For example, the quantizer 14 might provide a different frequency output each time the input heart beat rate changes by 10 heart beats per minute, so that one frequency is produced corresponding to an input frequency anywhere between 50 and 60 heart beats per minute, a second output frequency is produced corresponding to an input frequency anywhere within the range 60 to 70 heart beats per minute, and so on. An audio signal generator 16 energizing loudspeaker 17 provides an audio output from the quantized heart beat signal. As an example, a tone varying from 300 Hz. to 2,000 Hz. may be employed, varying in discrete steps to provide 28 different frequencies or tones according to a diatonic or other scale. In this fashion, minor variations in input signal do not produce a change in the output tone until the input signal passes from one quantized range into another. The output signal, changing in discrete steps, is easy to monitor, and the abrupt change in tone from one frequency to another will be easily recognized by a listener.

Figure 2B:
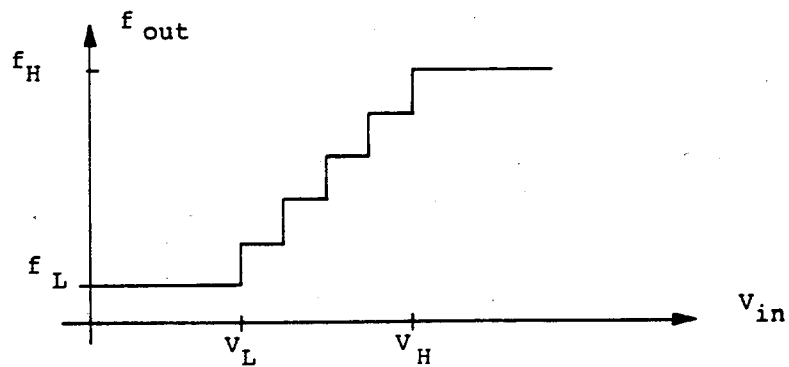

FIGS. 2A and 2B may be of assistance in understanding the quantizing taking place in the system of FIG. 1. These latter figures are the conversion characteristics of voltage to frequency converters. The first characteristic, shown in FIG. 2A, is linear, so that for an input variation in voltage between input voltages of $V_L$ and $V_H$ a corresponding output frequency varying linearly throughout the range $f_L$ and $f_H$ is produced. A characteristic as shown in FIG. 2B is what is found in a quantizer typically used in the system of FIG. 1. In particular, as input voltage (representing heart beat rate) varies over the range $V_L$ to $V_H$, the output frequency varies in steps over the range $f_L$ to $f_H$. In the curve shown in FIG. 2B, there are five equal discrete steps or changes in frequency within that range. It should be noted that the curves of FIGS. 2A and 2B are representative; the scales of the axes may be linear or nonlinear.

Turning to FIG. 3, a system is shown dealing with a number of different inputs for generating an output audible signal representative of those inputs. Input signals are provided at terminals 18, 20, 22, and 24, corresponding respectively to four different monitored conditions, such as pulmonary artery diastolic blood pressure, body temperature, heart rate and systolic blood pressure, to name some examples. A signal processor 26 receives the input signals and generates an audio signal from loudspeaker 27 having a plurality of different parameters, each of which corresponds to an individual one of the monitored input conditions. FIG. 3A shows a representative output signal from the signal processor 26, and it may be composed of a series of recurring pulses 28. As an example, the amplitude a of each pulse 28 may be representative of the monitored condition on the input terminal 18 (pulmonary artery diastolic blood pressure), the time duration b of each pulse 28 may be representative of the monitored input at the terminal 20 (body temperature), the periodicity of the pulse train or the time duration c between the onset of successive pulses 28 may be representative of the input condition signal at terminal 22 (heart rate), and finally the frequency d of the signal that defines each individual pulse 28, i.e., the pitch of each pulse, may be representative of the monitored input at the terminal 24 (systolic blood pressure). It is a simple matter for a technician or physician to listen to the output signal and detect variations in the output parameters just discussed. That task is rendered even easier by the quantizing of the signals, as desired, as described above. Representative ranges for the parameters discussed above may be 55 to 90 decibels for amplitude a, in steps greater than or equal to 3 dB; time duration b may be greater than or equal to 200 milliseconds; the time c between the onset of successive pulses, expressed in terms of pulse periodicity, may be 1 to 150 pulses per minute; and the pitch d of each individual pulse may range from 300 to 2000 Hz.

Figure 4A:
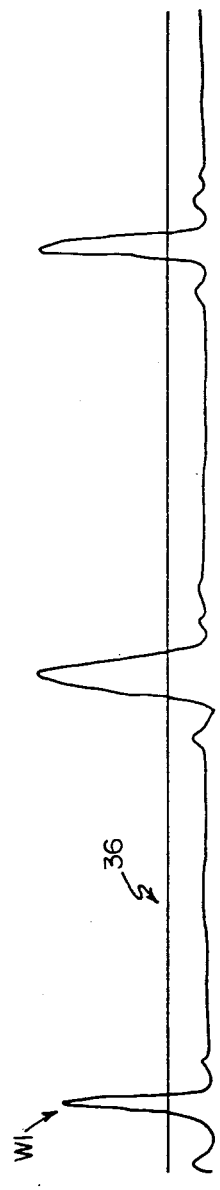
FIGS. 4A to 4E are waveform diagrams of signals at different points in the system of FIG. 4.

FIG. 4, with its accompanying waveform diagrams of FIGS. 4A to 4E, illustrates a system in accordance with FIG. 3 for monitoring a plurality of different inputs to produce an output audio signal, the parameters of which vary in accordance with the monitored inputs. An EKG signal at terminal 30 is from a conventional electrocardiograph (not shown), the waveform W1 of which is shown in FIG. 4A. The EKG signal is integrated by an integrator 32 to average or smooth that signal, which is applied as a trigger input signal to monostable multivibrator 34. In FIG. 4A, the signal level 36 denotes a threshold which must be exceeded by the signal from the integrator 32 to trigger the monostable multivibrator 34. The onset of the signal from the monostable multivibrator corresponds to the onset of each pulse 28 in FIG. 3A. The duration of the signal from the monostable multivibrator 34 is governed by a signal from integrator 38, which in turn receives an input signal at terminal 40 representative of body temperature, for example. Thus the duration of the pulse signal from the monostable multivibrator 34 is determined by body temperature, the body temperature signal being smoothed by integrator 38. The duration of the monostable multivibrator signal is represented in FIG. 3A by the width b of each pulse 28.

Figure 4B:
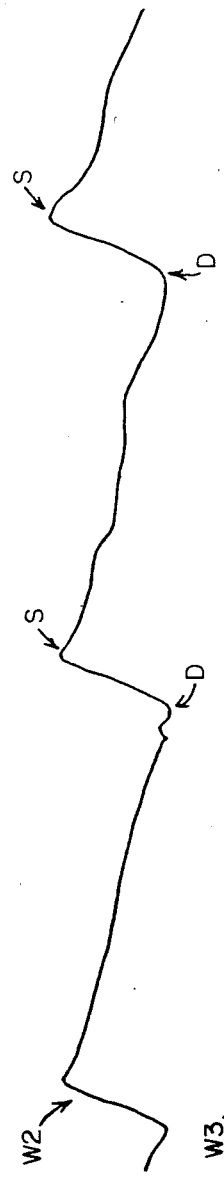
Figure 4C:
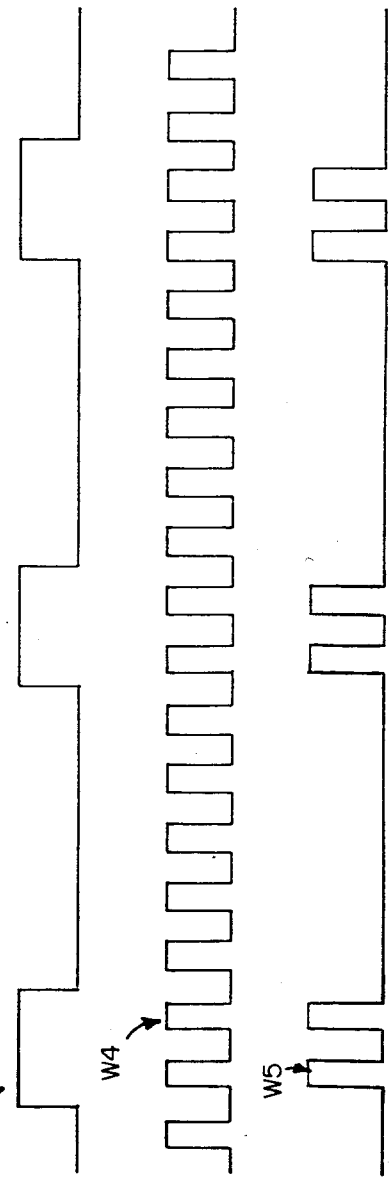
Figure 4D:
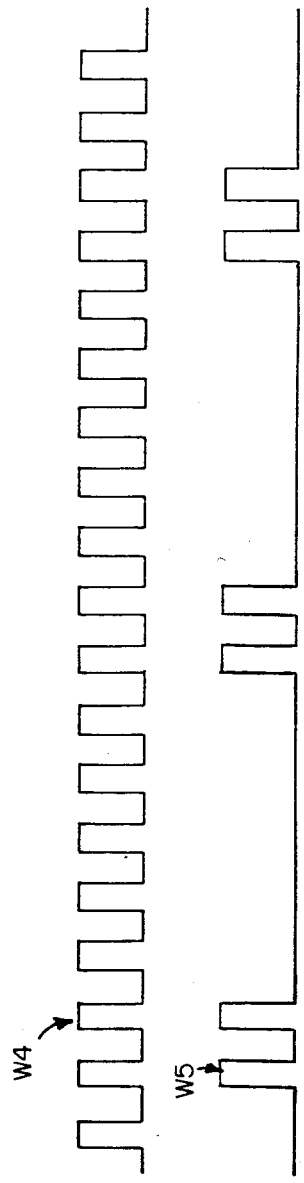
Figure 4E:
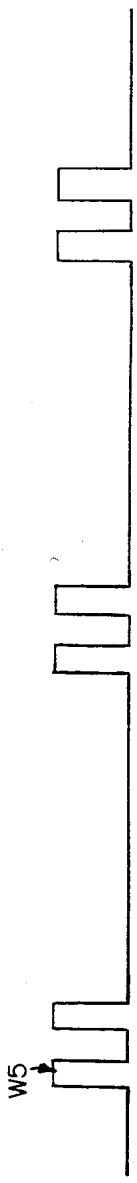

The signal from the monostable multivibrator 34, represented by the waveform W3 in FIG. 4C, is applied as one input to AND gate 42, which receives another input from a voltage to frequency converter 44. The converter 44 is coupled to an integrator 46 which in turn receives a signal from input terminal 48 representing, for example, systolic blood pressure. A representative blood pressure signal W2 is shown in FIG. 4B. The peaks of that signal, designated S in FIG. 4B, represent the systolic blood pressure, and may be developed by peak detection of the blood pressure signal W2. Accordingly, the integrator 46 smooths a signal representative of systolic blood pressure, which is converted in converter 44 to an output frequency. The voltage to frequency conversion characteristic of the converter 44 may be as shown in FIG. 2B, in accordance with a step function, so as to quantize the systolic blood pressure signal. The output signal from the voltage to frequency converter 44, represented by the waveform W4 in FIG. 4D, is applied, as noted, to the AND gate 42. The signal from the AND gate 42 thus has a waveform W5 as shown in FIG. 4E.

Thus, in this example, the AND gate 42 develops a series of recurring pulses, the periodicity of which is determined by a heart rate signal at the input terminal 30, the duration of each of which is determined by a body temperature signal at the input terminal 40, and the frequency of the signal defining each pulse being determined by a signal at the input terminal 48 representative of systolic blood pressure. The composite signal from the AND gate 42, of waveform W5 shown in FIG. 4E, is applied to an audio amplifier 50, having a gain which is determined by a signal from quantizing circuit 52, which in turn is supplied with a signal from integrator 54. The integrator 54 smooths an input signal from the terminal 56 representing pulmonary diastolic blood pressure, for example. Diastolic blood pressure is represented in FIG. 4B by the troughs D of a typical blood pressure signal processed conventionally to produce the diastolic blood pressure signal. The quantizing of the smoothed blood pressure signal may be done in any convenient fashion, for example, utilizing integrated circuitry to produce an output potential which varies in step fashion in accordance with a continuously varying input signal. The gain control of the audio amplifier 50 thus controls the amplitude of the output signal from the amplifier, i.e., the parameter a in FIG. 3A. The audio amplifier 50 thus energizes the loudspeaker 27 to generate an audio signal of the type shown in FIG. 3A, the parameters of which are representative of the various input conditions being monitored.

Thus a series of recurring pulses 28 as shown in FIG. 3A are produced by the system of FIG. 4, each pulse of which is constituted by a number of sub-pulses (w5 in FIG. 4E) which determine the pitch or frequency of the output pulse signal produced by the loudspeaker 27. The gain control signal from the quantizer 52 determines the amplitude of those pulses or the loudness of the signal from the loudspeaker. The repetition rate of the pulses in the train of successive pulses and the time duration of each pulse complete the parameters of the audio output signal produced by the loudspeaker 27. As noted above, it is a simple matter to train a technician or physician to recognize the varying parameters of the sound signal and to detect changes therein, especially if changes in those parameters are quantized so as to vary in step fashion as described above.

Presently preferred embodiments of the invention have been described, particularly in the field of monitoring body conditions. As noted above, the invention has application to other technical fields. For example, in the automotive field, engine speed and ignition dwell angle may be monitored, and periodicity (c in FIG. 3A) and frequency (d in FIG. 3A) of an audio signal may be varied in accordance therewith to provide meaningful information to an automotive technician without the need for visual inspection of conventional monitoring instruments.

Additionally, the preferred embodiments described above are obviously susceptible of modification by those skilled in the art. For example, four parameters of a recurring pulse signal (parameters a to d in FIG. 3A) have been disclosed as being variable. Some of these parameters may be rendered constant in any particular application. For example, in the automotive application noted above, periodicity and frequency are mentioned as an example of the type of variation that may occur. The other parameters of the pulse signal could be maintained constant.

Accordingly, the invention should be taken not as limited to the specific presently preferred embodiments which have been disclosed herein, but rather should be taken to be defined by the following claims.

I claim:

1. A system for providing a distinguishable audible output varying in accordance with a condition to be monitored comprising first means for generating a signal that varies in accordance with variations of a monitored condition, and audio signal generator means receiving said signal from said first means and generating an audible output that varies in n discrete steps corresponding to a range of variation of said signal.

2. A system according to claim 1, in which said audio signal generator means includes means for producing an audible output that varies in n discrete steps over a range of frequencies.

3. A system according to claim 2, in which said audio signal generator means includes means for producing said audible output in steps generally in accordance with a diatonic scale.

4. A system according to claim 1, in which said audio signal generator means includes means for producing an audible output which varies in n discrete steps over a range of amplitudes.

5. A system according to claim 1, in which said audio signal generator means includes means for producing an audible output which is a series of recurring pulses of sound, the duration of each pulse of which varies in n discrete steps over a range of pulse durations.

6. A system according to claim 1, in which said audio signal generator means includes means for producing an audible output which is a series of recurring pulses of sound, the pulse repetition rate of which varies in n discrete steps over a range of pulse repetition rates.

7. A system for providing an audible output varying in accordance with a plurality of different monitored inputs comprising first means for generating a plurality of signals representing a plurality of different monitored inputs, and audio signal generator means receiving said plurality of signals for generating an audio signal having a plurality of different audio parameters, each of said parameters corresponding to an individual one of said plurality of signals, said audio signal generator means includes at least one quantizer means for varying an associated parameter of said audio signal in n discrete steps corresponding to a range of variation in value of the corresponding one of said plurality of signals.

8. A system according to claim 7, in which said audio signal generator means includes means for producing an audio signal the parameters of which, that vary according to the monitored inputs are at least frequency and amplitude.

9. A system according to claim 7, in which said audio signal generator means includes means for producing an audio signal that is composed of a series of recurring pulses of which the parameters that vary according to the monitored inputs are at least two of the following:
 (a) amplitude of each pulse,
 (b) time duration of each pulse,
 (c) pulse periodicity,
 (d) frequency of signal defining each pulse.

10. A system according to claim 7, particularly suited for the monitoring of body conditions, in which said first means includes means for generating signals representative of at least two of the following:
 (a) heart rate,
 (b) systolic blood pressure,
 (c) pulmonary artery diastolic blood pressure,
 (d) body temperature.

* * * * *